(12) United States Patent
Whitledge

(10) Patent No.: US 6,342,253 B1
(45) Date of Patent: Jan. 29, 2002

(54) USE OF ESSENTIAL OILS TO REPEL AND TREAT HEAD LICE

(76) Inventor: Karen L. Whitledge, 14575 Harrison Rd., Romulus, MI (US) 48174

( * ) Notice: Subject to any disclaimer, the term of this patent is extended or adjusted under 35 U.S.C. 154(b) by 0 days.

(21) Appl. No.: 09/574,188

(22) Filed: May 18, 2000

Related U.S. Application Data

(60) Provisional application No. 60/134,690, filed on May 18, 1999.

(51) Int. Cl.[7] ........................ A61K 35/78; A61K 31/22; A61K 31/225; A01N 25/34
(52) U.S. Cl. ............... 424/736; 424/403; 424/DIG. 10; 514/546; 514/547; 514/918; 514/919
(58) Field of Search .................................. 514/918, 919, 514/546, 547; 424/195.1, 403, DIG. 10

(56) References Cited

U.S. PATENT DOCUMENTS

| | | | |
|---|---|---|---|
| 4,193,986 A | 3/1980 | Cox | 424/119 |
| 4,379,168 A | 4/1983 | Dotolo | |
| 4,587,123 A | 5/1986 | Price | 424/514 |
| 4,759,930 A | 7/1988 | Granirer | |
| 4,927,813 A | 5/1990 | Bernstein | |
| 5,106,622 A | 4/1992 | Sherwood | 424/514 |
| 5,411,992 A | 5/1995 | Eini | 514/424 |
| 5,591,435 A | 1/1997 | Vaccarello-Dunkel | 424/514 |
| 5,738,863 A | 4/1998 | Sackin | 424/514 |
| 5,888,984 A | * 3/1999 | Brown | 514/54 |
| 6,143,703 A | * 11/2000 | Cheung et al. | 510/101 |

FOREIGN PATENT DOCUMENTS

EP 945066 * 9/1999

* cited by examiner

*Primary Examiner*—Kevin E. Weddington

(57) ABSTRACT

Natural compositions of three essential oils effective as both a head lice repellent and treatment of *pediculosis capitis*. The compositions comprise essential anise oil present in an amount of about 3.5% to 50% by volume, essential tea tree oil present in an amount of about 2.5% to 40% by volume, and essential lemon oil present in an amount of about 2% to 20% by volume, the active agent can be combined with a pharmaceutically and/or cosmetically acceptable carrier for topical administration, such as aqueous or alcohol solutions, a gel, or a cream and administered with or without additives such as preservatives, antioxidants, fragrances, agents increasing solubility or delaying release of active agents. The active agent in concentrated form can be added to shampoos, hair sprays, rinses, styling gels or other personal preference haircare products. The active agent can also be used to treat material such as bedding, hair bows, headbands, caps, hats, helmet liners, brushes, and combs.

11 Claims, No Drawings

USE OF ESSENTIAL OILS TO REPEL AND TREAT HEAD LICE

REFERENCE TO RELATED APPLICATIONS

This application is entitled to the benefit of the filing date of provisional application No. 60/134,690 filed May 18, 1999.

BACKGROUND FIELD OF INVENTION

This invention relates to natural compositions and methods that both repel head lice and treat *pediculosis capitis*.

BACKGROUND TO THE PRESENT INVENTION AND PRIOR ART

Head lice infestation (*pediculosis capitis*) is a major problem in the United States, throughout Europe and Asia. In the United States alone 10 million cases of *pediculosis capitis* occurred in 1989. Lice are external parasites of warm blooded animals. They spread by crowding and sharing of personal items such as combs, hats, brushes and clothing.

Humans are host to three different types of lice, 1) head lice, 2) body lice, 3) crab or pubic lice.

The head louse has been among humans since their earliest origins. The louse has evolved in a highly specialized manner for survival on the haired human scalp, to the extent that its survival requires it to spend its entire life-cycle on a human host.

The life cycle of the head louse falls into three phases, egg, nymph and mature louse.

Louse eggs, some 0.5 to 0.8 by 0.3 millimeters, are usually laid at the base of hairs, within 0.5 mill of the scalp, where they hatch after seven or eight days. During incubation, the hair will grow away from the scalp by some two millimeters. The eggs are firmly glued to the hair, usually one per hair, by a clear, quick-setting substance secreted by the female. Live eggs are usually camouflaged by being the same color as the scalp.

The nymph resembles the adult louse in behavior, and in physical terms apart from size. In about ten days after hatching it is mature.

Mature head lice are 2 to 4 millimeters long, shun light, and move swiftly—10 to 20 centimeters a minute—in all lateral directions, clinging to and crawling through the hair with their six claws. Otherwise transparent, head lice camouflage themselves by darkening, after feeding, to the color of the skin and hair of the host, in the range from blond to black.

The empty egg-shell is called a nit. It is white in color, and remains firmly glued to the hair. The hair grows at a rate of some one centimeter per month, carrying any nits attached to it away from the scalp.

The characteristic feature of the group to which human head-lice belong is blood-sucking. To feed, the louse pierces the scalp with its mouth-parts, pumping in saliva and drawing out a mixture of saliva and blood. While humans are not born with the ability to react to such bites, repeated contact with the sensitizing allergens contained in the saliva creates an allergic reaction, so that each further bite evokes an itchy reaction. Wounds produced in the scalp by scratching in response to itches can become inflamed and infected. If louse infestation is allowed to persist, the wounds can develop an extreme condition, wherein successful treatment cannot be assured.

A population of head lice which is neglected will reach a steady state, where the death-rate equals the birth-rate, and some two hundred lice of all post-ovum stages are present. About five thousand eggs are laid each month and the head eventually becomes grey with drifts of empty egg shells. Such a population, when present for some months, is enough to produce the symptoms of *pediculosis capitis*. The child becomes itchy, tired, dull and sullen. The bright child becomes average, and the average child stupid.

Although they can be shown to act as transmitters of typhus and fevers in the laboratory, head lice are not responsible for the transmission of disease in the field. Lice are considered highly unlikely to transmit AIDS.

The highest incidence of *pediculosis capitis* is found in children between the ages of five and fifteen years. In the developed world head lice are most prevalent among suburban and rural children.

Even though people experience unpleasant sensations as a result of louse infestation, they often deny *pediculosis capitis* because of feelings of disgust and shame. Lice infestation used to be thought of as a problem only of the poor or poorly housed. It is now abundantly clear that the problem of head lice has extended to a very large number of middle class homes in the western world and this leads to increasing numbers of consultations with family practitioners or pharmacists who advise as to the treatment currently being recommended.

Other general recommendations include machine washing in hot water (over 54° C.) or dry cleaning all clothing, including coats, hats, scarves, pillow cases, towels, and bedding materials, which may have contacted an infested individual.

Several products for treating *pediculosis capitis* are available over the counter, the most widely used products in this category include Rid® Lice Killing Shampoo (Pfizer), Nix® Cream Rinse and A-2000® Shampoo Concentrate which contains pyrethins and piperonyl butoxide as active ingredients. Prescription drugs include Ovidem® (active ingredient 0.5% malathion) and Kwell® (containing landane 1%).

Pediculicides, selectively kill lice which invade the epidermis. Although a number of brands contain either carbaryl or malathion, lotions containing phenothrin and permethrin are now the major products. These are pyrethroid compounds are highly effective insecticidal neurotoxins, with efficacy against both adult lice and their eggs. Permethrin (3-phenoxyphenyl)methyl (+/-) cis/trans 3-(2,2-dichloroethenyl)2,2-dimethylcyclopropanecarboxylate, is used as a 0.5% preparation in a paraffin base. Other actives are benzyl benzoate and crotamiton. All are applied topically. The manufacturers claim appropriate use does not lead to resistance but evidence now would seem to suggest otherwise. Many health authorities are now advising no active treatment because of problems apparently due to resistant lice. Instead they recommend over-conditioning the hair and regular use of a specially designed lice comb.

It is clear that a repellent, which curtails infestation, is preferable. A number of insect repellents have been developed, however most are not specific for lice. Several natural repellents are specific for mosquitoes or fleas, U.S. Pat. No. 5,106,622 teaches a natural repellent effective against mosquitoes and ticks, U.S. Pat. No. 5,738,863 teaches a honey bee repellent comprising tea tree oil, U.S. Pat. No. 5,411,992 teaches a lice repellent comprising terpenoids. This survey shows that there is no teaching of the invention, which is a topical, natural composition useful as both a lice repellent and a treatment of *pediculosis capitis*.

The following U.S. patents are considered relevant:

U.S. Pat. No. 4,193,986
U.S. Pat. No. 4,587,123
U.S. Pat. No. 5,591,435
U.S. Pat. No. 4,927,813
U.S. Pat. No. 5,411,992
U.S. Pat. No. 4,759,930
U.S. Pat. No. 5,208,029
U.S. Pat. No. 4,933,371
U.S. Pat. No. 4,193,986
U.S. Pat. No. 5,783,863
U.S. Pat. No. 4,379,168
U.S. Pat. No. 5,106,622

SUMMARY OF THE INVENTION

It has been discovered that the combination of three essential oils: anise, tea tree and lemon, in a concentration of between 0.01% and 50%, most preferably between 0.01% and 10%, is a very good head lice repellent and treatment of pediculosis capitis.

The active agent can be combined with a pharmaceutically and/or cosmetically acceptable carrier for topical administration, such as an aqueous or alcohol solution, a gel, or cream, and administered with or without additives such as preservatives, antioxidents, fragrances, agents increasing solubility or delaying release of active agents.

The active agent in concentrated form can be added to personal preference shampoos, hair-sprays, rinses, styling gel or other personal preference hair care products.

The active agent can also be used to treat material such as hairbows, headbands, caps, hats, helmet linings, any object that is made of cloth and worn on the head.

The active agent can also be used as a head lice repellent and treatment of pediculosis capitis for animals.

Other objects, features and advantages of the present invention will become apparent to those skilled in the art from the following detailed description. It is to be understood however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

OBJECTS AND ADVANTAGES

Accordingly, besides the objects and advantages of the compositions and methods described in this patent, several objects and advantages of the present invention are:

a) To provide a novel, low cost, combination head lice repellent and treatment of pediculosis capitis.

b) To provide a natural, non-toxic head lice repellent and treatment of pediculosis capitis desirable for health and environmental concerns.

c) To provide a non-irritating head lice repellent and treatment of pediculosis capitis.

d) To fill a market void by offering a head lice repellent that has the potential to curtail epidemics of pediculosis capitis.

e) To provide an easy-to-use head lice repellent and treatment of pediculosis capitis.

f) To eliminate, by the use of the repellent, the need to purchase additional costly products and extend considerable effort exterminating lice and nits from bedding, clothing, furnishings, etc.

g) To provide a head lice repellent that does not kill insects, thus, populations of target insects will not select as readily for resistance to the repellent.

h) To provide a novel method of utilizing a head lice repellent.

i) To provide a head lice repellent and treatment for pediculosis capitis in concentrate form that can be easily combined with the users personal preference of hair care products.

DETAILED DESCRIPTION OF THE PREFERRED EMBODIMENTS

Natural anise oil is an essential oil of the family ammiaceae (carrot family), anise (*pimpinella anisum*) is a herb having a strong odor and bearing seeds from which is distilled the aromatic oil of anise. The flavoring is used in liqueurs and some bakery products and confections. It is non-toxic and non-irritating to the skin. See, *Van Nostrands Scientific Encyclopedia* 5th Edition P.156.

Natural tea tree oil is an essential oil of the tea tree, *melaleuca alternifolia,* which is native to eastern Australia. It is non-irritating to the skin and non-toxic. Tea tree oil has long been known as being useful as, for example, a machine cutting oil, perfumery toner, flavoring and antiseptic agent and antimicrobial agent. See, e.g., Brophy et al., J. Agric. Food Chem. 37:5, pp. 1330–35 (1989) (Analysis of the tea tree oil); Olsen, *Australian Tea Tree Oil* (Kali Press 1989).

Natural lemon oil is an essential oil of the rutaceae family. A small evergreen tree, native to Asia, but has become naturalized in the Mediterranean region. It is cultivated in many parts of the world, with most of the oil being produced in Italy, Cyprus, Israel and California. The oil is extracted from cold compression of the peel of the fruit. The aroma is fresh and sharp just like the fresh fruit. Lemon oil has the following properties: anti-anaemic, antimicrobial, antirheumatic, antiseptic, antispasmodic, antitoxic, astringent, bactericidal, carminative, cytophylactic, cicatrisant, depurative, diuretic, febrifugal, haemostatic, hypotensive, insecticidal, rubefacient, sudorific, tonic, vermifugal. See, Wildwood, C., *The Encyclopedia of Aromatherapy,* pp 271 (1996).

Surprisingly, it has now been discovered that essential anise oil, essential tea tree oil, and essential lemon oil can be combined to produce a highly effective, non-toxic head lice repellent and *pediculosis capitis* treatment composition that contains no harsh chemicals, is environmentally friendly, can be applied topically to humans or animals, and repels or kills insects.

Essential anise oil, essential tea tree oil and essential lemon oil are present in the invention in amounts effective to both repel head lice and treat *pediculosis capitis.*

Preferably, essential anise oil is present in an amount from about 3.5% to 25%, more preferably about 3.5% to 10% for repellent, and 9% to 20% for treating *pediculosis capitis.*

Preferably, essential tea tree oil is present in an amount from about 2.5% to 20%, more preferably about 3.5% to 7% for repellent, and 7% to 20% for treating *pediculosis capitis.*

Preferably, essential lemon oil is present in an amount from about 2% to 15%, more preferably about 2% to 7% for repellent, and 4% to 9% for treating *pediculosis capitis.*

The essential oils in this invention can be obtained commercially, for example, from Frontier Natural Products Co-op, Norway, Iowa U.S.

Although the SD alcohol contained in the following examples is used as a carrier and not wishing to be bound to any particular theory, I believe it has properties that are active in the treatment of *pediculosis capitis* contained in this invention.

The head lice repellent and treatment of *pediculosis capitis* can be prepared in various forms, such as an aqueous solution, an alcohol solution, a cream, a powder, a gel, a rinse, a spray, hair styling mousse, shampoo, and conditioner.

The head lice repellent and treatment of *pediculosis capitis* can be delivered in various forms, such as a pump, spray mist, an aerosol spray, a rinse, or a pump spray or liquid dip for brushes, combs, and treated material, such as fabric.

Sprays, for example, can be prepared using conventional propellants, such as propane, butane, isobutane, either alone or in various mixtures known to those skilled in the art.

Typical liquid carriers useful in preparing both repellent and treatment according to the invention include water, alcohols, such as methyl, ethyl, propyl and isopropyl alcohol, glycols, ketones, ethers, hydrocarbons, etc. Appropriate amounts of the liquid carrier can be readily determined by those skilled in the art. For example, when alcohols are used as liquid carriers, they can be present in amounts from about 5% to 90%, in particular 10% to 60%.

Exemplary additives useful in the invention include vitamin E, fragrances, emulsifiers, pH adjusting agents, waxes, antimicrobial agents, preservatives, antioxidents, agents increasing solubility or delaying release of active agents, etc.

The formulations according to the invention can safely be applied to the skin of a human or animal, and can be applied to clothing or other porous or non-porous surfaces.

The following non-limiting examples illustrate the repellent and treatment compositions according to the invention and are set forth in volume percentages.

EXAMPLE 1

Repellent pump spray for topical use

To SD alcohol 40 (200 proof) (50.00%) are added essential anise oil (4.50%) essential tea tree oil (3.50%) essential lemon oil (2.00%) water (38.00%) fragrance (2.00%).

EXAMPLE 2

Repellent aerosol spray

To SD alcohol 40 (200 proof) (88.00%) are added essential anise oil (4.50%) essential tea tree oil (3.5%) essential lemon oil (2.00%) fragrance (2.00%).

Exemplary propellants include the following:

a) For use on skin and sensitive areas: 85% isobutane, 15% propane. Pressure 45 psig at 70° C.

b) For use on clothing, furnishing, and physical environments: 50% butane, 50% propane. Pressure 70 psig at 70° C.

EXAMPLE 3

Repellent pump spray or liquid dip for fabric

To SD alcohol 40 (200 proof) (50%) are added essential anise oil (9.00%) essential tea tree oil (7.00%) essential lemon oil (4.00%) water (28.00%), fragrance (2.00%).

EXAMPLE 4

Rinse—A *pediculosis capitis* treatment

To SD alcohol 40 (200 proof) (50.00%) are added essential anise oil (9.00%) essential tea tree oil (7.00%) essential lemon oil (4.00%) water (28%) fragrance (2.00%).

EXAMPLE 5

Repellent pump spray—For topical use

To a 7 ounce bottle of hair spray is added 10 drops (10M) of essential anise oil, 7 drops (7M) of essential tea tree oil, 3 drops (3M) of essential lemon oil.

EXAMPLE 6

A concentrate comprising 45% essential anise oil, 35% essential tea tree oil and 20% essential lemon oil.

Usage of Examples

Examples 1, 2 and 5 are for use as a repellent to repel head lice from an individual already free of lice and nits. It is held 5" to 8" from the head and sprayed or misted lightly and evenly.

Example 3 is a repellent for spraying or dipping fabrics such as, but not limited to, headbands, sweatbands, barrettes, scarves, hair bows, hair ties, caps, helmet liners, hats, or hat liners. These, when treated and worn, will act as a repellent.

Example 4 is for treatment of *pediculosis capitis* to be applied as follows:

a) Saturate the head.

b) Cover with shower cap for 10 to 15 minutes.

c) Shampoo hair.

d) Rinse with vinegar.

e) Comb through hair to remove any remaining nits.

The following case studies were carried out on children at the parents request and with their permission.

Case Study 1

Subject 1 is an eight year old living in Romulus, Mich., attending Halecreek Public Elementary School. Subject 1 had contracted *pediculosis capitis* seven times between February 1997 and August 1998. The subject was treated with daily applications of Example 1 from Aug. 1, 1998 through Nov. 30, 1998 and daily applications of Example 5 from Dec. 1, 1998 through May 1, 1999. The subject was known to have been exposed to head lice during treatment on twelve occasions, both at school and socially. The subject remained free of head lice during the entire treatment period from Aug. 1, 1998 through May 1, 2000.

Case Study 2

Subjects 2, 3 and 4, ages four, six and eight respectively, reside in the same household in Taylor, Mich., and attend Taylor Parks Public Elementary School. Subjects 2, 3 and 4 had contracted *pediculosis capitis* three times between October 1997 and October 1998. The subjects were treated with daily applications of Example 1 from Nov. 1, 1998 through Mar. 1, 1999, and daily applications of Example 5 from Mar. 2, 1999 through May 1, 2000. The subjects were known to have been exposed to head lice during treatment on thirty-eight occasions (collectively), both at school and socially. The subjects remained free of head lice during the entire treatment period from Nov. 1, 1998 through May 1, 2000.

Case Study 3

Subjects 5 and 6, ages six and eleven, respectively, reside in the same household in Taylor, Mich., and attend Taylor Parks Public Elementary School. Subjects 5 and 6 had contracted *pediculosis capitis* approximately fourteen times between December 1997 and October 1998. The subjects were treated with daily applications of Example 1 from Nov. 1, 1998 through Mar. 1, 1999, and daily applications of Example 5 from Mar. 2, 1999 through May 1, 2000. The subjects were known to have been exposed to head lice during treatment on thirty-four occasions (collectively), both at school and socially. The subjects remained free of head lice during the entire treatment period from Nov. 1, 1998 through May 1, 2000.

Case Study 4

Subject 7 is an eight year old living in Detroit, Mich. and attends Bennett Public Elementary School. Subject 7 had contracted *pediculosis capitis* approximately twelve times between December 1997 and October 1998. The subject was treated with daily applications of Example 1 from Nov. 1, 1998 through Mar. 15, 1999. The subject was known to have been exposed to head lice during treatment on nineteen occasions, both at school and socially. The subject remained free of head lice during the entire treatment period from Nov. 1, 1998 through Mar. 15, 1999. As treatment was stopped by Mar. 16, 1999, the subject contracted *pediculosis capitis* on Mar. 28, 1999 and had four additional outbreaks prior to May 1, 1999.

Case Study 5

Subject 8 is an eight year old living in Detroit, Mich., attending Harms Public Elementary School. Subject 8 was unsuccessfully treated twice for *pediculosis capitis* using different brands of toxic treatment currently on the market. The head lice appeared to be of a particularly resistant strain. The subject was subsequently treated successfully with Example 4.

There were no reports of sensitivity or adverse reactions.
Conclusion, Ramifications, and Scope The foregoing case studies show that the composition described herein is effective in both repelling head lice and treating *pediculosis capitis*. In every case, the subjects were completely satisfied with the invention. There were no reports of irritations, allergic reactions, photo sensitivity or any other irregular occurances.

Thus the compositions described above are useful for repelling head lice and treating *pediculosis capitis*. The fact that it is effective on humans would have the skilled artisan to conclude that efficacy would be expected with domestic animals, including pets. Hence, a method for repelling head lice and treating *pediculosis capitis* is taught, wherein the above compositions are used by spraying them on the hair, applying them to the scalp or wearing treated head dressings.

As efficacy on a living subject is less predictable than is efficacy on inanimate material, the foregoing results suggest that the repellent compositions are also effective as a repellent for inanimate material such as clothing, furniture, and so forth.

The terms and expressions which have been employed are used as terms of description and not limitation, and there is no intention in the use of such terms and expressions of excluding any equivalents of the features shown and described or portions thereof, it being recognized that various modifications are possible within the scope of the invention.

What is claimed is:

1. A method to repel head lice, comprising applying topically to a human susceptible to lice infestation an effective amount to repel but not kill lice of a mixture in an acceptable carrier for topical application wherein the active ingredients comprise about 2% to 10% by volume, of natural active ingredients consisting of essential anise oil present in an amount of about 1.5% to 25% by volume, essential tea tree oil present in an amount of about 1.0% to 20% by volume, and essential lemon oil present in an amount of about 1.0% to 15% by volume.

2. The method of claim 1, wherein said carrier is a material selected from the group consisting of an aqueous solution, an alcohol solution, gel, cream, rinse, powder, spray, shampoo, conditioner, and hair styling mousse.

3. The method of claim 1, wherein said carrier further comprises a compound selected from the group consisting of antioxidants, antimicrobials, preservatives, fragrances, and substances delaying dissolution of essential oils.

4. A method to kill head lice and nits comprising applying to a human thusly infested, an effective amount to kill lice and nits, of an essential oil mixture in an acceptable carrier for topical application, wherein the active ingredients comprise about 3% to 15% by volume, of natural active ingredients consisting of essential anise oil present in an amount of about 2.5% to 25% by volume, essential tea tree oil present in an amount of about 2.0% to 20% by volume, and essential lemon oil present in an amount of about 1.0% to 15% by volume.

5. The method of claim 4, wherein said carrier is a material selected from the group consisting of an aqueous solution, an alcohol solution, gel, cream, rinse, powder, spray, shampoo, conditioner, and hair styling mousse.

6. The method of claim 4, wherein said carrier further comprises a compound selected from the group consisting of antioxidants, antimicrobials, preservatives, fragrances, and substances delaying dissolution of essential oils.

7. A method to repel lice, comprising applying to an animal susceptible to lice infestation an effective amount to repel, but not kill lice, of a mixture in an acceptable carrier for topical application, wherein the active ingredients comprise 2% to 10% by volume, of natural acting ingredients consisting of essential anise oil present in an amount of about 1.0% to 20% by volume, essential tea tree oil present in an amount of about 1.0% to 25% by volume, and essential lemon oil present in an amount of about 1.0% to 15% by volume.

8. The method of claim 7 wherein said carrier is a material selected from the group consisting of an aqueous solution, an alcohol solution, gel, cream, rinse, powder, spray, shampoo, conditioner, and hair styling mousse.

9. The method of claim 7 wherein said carrier further comprises a compound selected from the group consisting of antioxidants, antimicrobials, preservatives, fragrances, and substances delaying dissolution of essential oils.

10. A method to repel head lice, comprising applying to cloth or fabric, headbands, bows, sweatbands, barrettes, scarves, ties, caps, helmet liners, hat liners and hats, an effective amount to repel, but not kill head lice, of a mixture in an acceptable carrier, wherein the active ingredients comprise about 3% to 20% by volume, of natural ingredients consisting of essential anise oil present in an amount of about 2.5% to 25% by volume, essential tea tree oil present in an amount of about 2.0% to 20% by volume, and essential lemon oil present in an amount of about 1.0% to 15% by volume, the various head dressings when worn provide the repellent.

11. A method to repel head lice and treat *pediculosis capitis* wherein the active ingredients consist of a concentrate of an essential anise oil present in an amount of about 20% to 50% by volume, essential tea tree oil, present in an amount of about 10% to 40% by volume, and essential lemon oil present in an amount of about 10% to 35% by volume, wherein the concentrate is then added to shampoos, hair sprays, rinses, styling gels or other personal preference haircare products.

* * * * *